US006333357B1

(12) United States Patent
Eig

(10) Patent No.: US 6,333,357 B1
(45) Date of Patent: Dec. 25, 2001

(54) BEHAVIOR CHEMOTHERAPY

(75) Inventor: Mark H. Eig, Chevy Chase, MD (US)

(73) Assignee: Be Able, LLC, Chevy Chase, MD (US)

(*) Notice: Subject to any disclaimer, the term of this patent is extended or adjusted under 35 U.S.C. 154(b) by 0 days.

(21) Appl. No.: 09/434,286

(22) Filed: Nov. 5, 1999

(51) Int. Cl.$^7$ ............... A61K 31/135; A61K 31/445; A61K 31/35

(52) U.S. Cl. ............ 514/646; 514/654; 514/456; 514/319; 514/810; 514/811; 514/812

(58) Field of Search .................... 514/646, 654, 514/456, 319, 810, 811, 812

(56) References Cited

U.S. PATENT DOCUMENTS 4,255,439 * 3/1981 Cooper ........................ 424/273
4,999,382 * 3/1991 Wurtman et al. ............. 514/646

FOREIGN PATENT DOCUMENTS

2248392A * 8/1992 (GB) .

OTHER PUBLICATIONS

Wu, Risheng "Clonidine sticking sheet and nicotine sticking sheet compound smoking stopping method" Faming Zhuanli Shenqing Gongkai Shuomingshu, 1998: 243491 5pp.*

Sellers et al. "Do serotonin uptake inhibitors decrease smoking? Observations in a group of heavy drinkers." Journal of Clinical Psychopharmacology, ISSN: 0271–0749, (1987 Dec.) 7 (6) 417–420.*

Hoffman et al., "Catecholamines, Sympathomimetic Drugs, and Adrenergic Receptor Antagonists," Goodman & Gilman's The Pharmacological Basis of Therapeutics (Ninth Ed., McGraw Hill) Chapter 10:199–242.

Noble et al., "Citalopram A Review of its Pharmacology, Clinical Efficacy and Tolerability in the Treatment of Depression," CNS Drugs (1997) 8(5):410–431.

Physicians' Desk Reference (52 Edition, Medical Economics Co. 1998) 974–975, 2161–2164, 2420–2422, 3209.

Physicians Genrx (Mosby–Year Book, Inc., St. Louis, Mo. 1996) 1675–1677, 859–860.

Rogers et al., "Long–term Efficacy and Safety of Donepezil in the Treatment of Alzheimer's Disease: An Interim Analysis of the Results of a US Multicentre Open Label Extension Study," European Neuropsychopharmacology (1998) 8:67–75.

Rogers et al., "The Efficacy and Safety of Donepezil in Patients with Alzheimer's Disease: Results of a US Multicentre, Randomized, Double–Blind, Placebo–Controlled Trial," Dementia (1996) 7:293–303.

Scates et al., "Focus on Citalopram: A Selective Serotonin Reuptake Inhibitor for the Treatment of Depression," Formulary (1998) 33:725–743.

* cited by examiner

*Primary Examiner*—Theodore J. Criares
*Assistant Examiner*—Jennifer Kim
(74) *Attorney, Agent, or Firm*—Morrison & Foerster LLP

(57) ABSTRACT

A protocol for permanent modification of behavior and elimination of undesired habits is described. The protocol involves stimulating the implicit memory, followed by continuing such stimulation in conjunction with psychological treatments followed by continuing said stimulation of the implicit memory and, in addition, stimulating the explicit memory. Use of this protocol results in a permanent replacement of undesirable behaviors with desirable ones.

11 Claims, No Drawings

BEHAVIOR CHEMOTHERAPY

TECHNICAL FIELD

The invention relates to modification of behavior, particularly habitual or addictive behavior, using a combination of chemotherapeutic assistance and psychological counseling. More specifically, it relates to a three-stage protocol for replacing an undesired habit with a desired one.

BACKGROUND ART

Attempts to alter human behavioral patterns associated with addictions or compulsions are littered with failure. Programs designed to modify such habits as overeating, addiction to narcotics, alcoholism, and smoking are the basis for an industry with a turnover of billions of dollars a year. Some of these programs involve entirely psychological counseling and support. Others employ known chemical agents.

A large number of pharmacological agents that affect behavior is known. Perhaps one of the best known is the combination Fen-Phen used for many years to exert an anorectic effect to treat obesity. This combination of phentermine and fenfluramine was available until recently when the cardiopulmonary side effects of this medicament were considered unacceptable. Both of these components are related to amphetamines and are epinephrine analogs which can be used to combat fatigue and drowsiness. The use of, for example, donepezil to treat the symptoms of Alzheimer's disease is also known. In short, a variety of agents known to affect the central nervous system have been used in various contexts to treat a number of indications related directly or indirectly to behaviors.

At present, however, there appears to be no established treatment that is adaptable generally to replacing undesired behaviors permanently with desired ones. The present invention provides such a protocol.

DISCLOSURE OF THE INVENTION

The invention provides a protocol that can be adapted to replace a behavioral pattern that is ingrained and undesired with a desired one—the desired behavior may include simply avoidance of the undesirable activity. The protocol can be applied to humans and to other mammals. The protocol of the invention can be modified as described herein to treat individuals who are habitual gamblers, smokers, alcoholics, sufferers of incapacitating fatigue, narcotics addicts, and the like. It can also be used to train animals, such as domestic pets. It is a three-stage protocol the length of which will vary with the nature of the subject treated.

The first stage comprises acute treatment with effective amounts of compounds that augment the activity of and generally affect the amine neurotransmitters that are associated with the sympathetic nervous system and which influence implicit memory. This treatment may be supplemented with specific aids as dictated by the condition of the subject; for example, a nicotine patch may be useful where the undesired behavior is smoking.

The second stage involves maintaining chemotherapy with these amine neurotransmitter augmenting compounds but adds a component of psychology/supportive therapy in the case of humans, and training or otherwise effecting or conditioning a behavioral adjustment in the case of nonhuman animals. For nonhuman animals this may involve an indirect intervention, e.g., modifying the behavior of the owner.

The third stage comprises administering an acetylcholinesterase (AChase) inhibitor along with the compounds described above with respect to stages I and II. The third stage mimics the psychological condition of rapid eye movement (REM) sleep.

MODES OF CARRYING OUT THE INVENTION

The subjects for which the invention protocol is intended are human or animal subjects who would be benefited by modification of behavior to overcome what might simply be called a "bad habit." The habits can be internal or external. An internal habit arises by virtue of repetitive behavior unrelated to a direct metabolic effect of an external agent. An external habit further involves an interaction with an external metabolic agent. External habits include narcotics addiction and smoking; internal habits would be exemplified by gambling and overeating. Of course, external habits may be reinforced by an internal habit mechanism as well. As will be seen, where a habit is internal, stage I treatment consists only of stimulators of the sympathetic nervous system in the form of compounds that stimulate amine neurotransmitters, optionally along with agents to control possible side effects of these drugs in cases where they are needed. For treatment of habits which have an external component, however, the subject is supplied with sufficient amounts of the external substance, or with a specific substitute therefor, to ameliorate withdrawal symptoms.

In general, the habitual behavior is controlled by "implicit memory." As defined herein, "implicit memory" is the unintentional recall of events or activities that influence behavior. Implicit memory is controlled by amine neurotransmitters, most prominently serotonin, norepinephrine, and dopamine. Implicit memory is brought to bear in behaviors that are permanently available and relatively unconsciously controlled. Exemplary behaviors of this type often include a physical component. Motor skills such as riding a bicycle, skiing, swimming, ice skating and the like, once learned, are essentially permanent. Conscious mechanisms are not required to bring them to recall.

On the other hand, "explicit memory" as defined herein relates to a conscious and deliberate recall of recent events and volitional behavior. In general, this type of memory is controlled by a single neurotransmitter, acetylcholine. In stage III of the protocol described herein, the explicit memory is stimulated along with the implicit memory, thus mimicking the transfer of elements from explicit to implicit memory similar to that which occurs in REM sleep. This transfer, in general, permits replacement of a "good" habit which has been implanted in the explicit memory into the habitual realm of the implicit memory. Thus, the behavior patterns explicitly learned in stage II of the invention protocol are transferred into the implicit memory in stage III.

As set forth above, the method of the invention is a protocol that involves three stages of treatment. The first stage, initial therapy, is designed to activate the implicit memory to make the habitual behavior available for modification. The pharmacological agents useful in this stage are compounds that stimulate amine neurotransmitters of the sympathetic nervous system. In general, these compounds are amines which are related to the three major neurotransmitters, serotonin, norepinephrine, and dopamine. Included among these are compounds related to norepinephrine such as ethylnorepinephrine, metaraninol, tyramine, hydroxyamphetamine, methoxamine, albuterol, metamphetamine, benzphetamine, phenylpropanolamine, phentermine, fenfluramine (Pondamin) and dexfenfluramine (Redux), diethylpropion, phentriazine and phendimetriazine. Preferred among these is a combination of phentermine (Ionamin, Adipex) and fenfluramine (Pondamin).

Also useful in stage I is administration of a selective serotonin reuptake inhibitor (SSRI) such as citalopram (Celexa), fluoxetine HCl (Prozac), fluoxamine maleate (Luvox), paroxetine HCl (Paxil) and sertraline HCl (Zoloft). Also useful are drugs which affect dopamine receptors, such as apomorphine and its derivatives.

The dosage of the compounds administered to stimulate the sympathetic nervous system and implicit memory will depend on the specific pharmacologic agent chosen, the condition of the subject, and the judgment of the physician or veterinarian. However, for the combination of phentermine and fenfluramine, preferred dosage ranges are approximately 10 mg fenfluramine and 15–30 mg of phentermine daily. Typical dosages of citalopram are of the order of 10 mg daily.

In addition to the general implicit memory stimulators of the types set forth above, supplemental medication may also be indicated. Where the subject shows severe dependency, or is desirous of modifying a multiplicity of habits, an adrenergic agonist selective for the $\alpha_2$ receptor is also desirable. These compounds are typically imidazolines and are typified by clonidine. The effects of clonidine appear to result from activation of the $\alpha_2$ receptors in the lower brain stem region, and clonidine has been used previously in treating subjects addicted to drugs, alcohol and tobacco. Clonidine is considered to help ameliorate adverse sympathetic nervous activity associated with withdrawal from these agents. If clonidine is used, typical dosage levels are on the order of 0.1–0.4 mg orally, daily. It can also be administered as a patch.

Other supplementary medications which are employed in stage I are specific for particular addictions. Thus, a nicotine patch may be useful where the habit to be shed is smoking; a low-dose nicotine patch which provides 7 mg is typical, alternate dosage levels can also be used. If the habit to be shed is alcoholism, a supplementary dose of benzodiazapine may also be helpful.

For treatment of obesity due to overeating, the subject is generally placed on a low-calorie or very-low-calorie diet. One such diet is marketed as Nutrimed which is a high-protein, low-carbohydrate, semistarvation fast. The standard protocol for providing Nutrimed regimens utilizes five "milkshake" like compositions per day to supply 420 kC. It is helpful to modify this regimen to include, as a substitute for one or two of the "shakes," a small meal so that the subject can experience the social interaction associated with dining. The inclusion of this modification has been helpful in ensuring compliance. The use of this regimen, modified or unmodified, is also sometimes helpful in subjects who are not obese and inclusion of this regimen in the therapeutic protocol has been found successful in a number of instances.

In general, very low calorie diets generally successfully block hunger driven by habit rather than by appetite. Such habit-driven hunger is an example of behavior controlled by implicit memory but governed by an external metabolic agent. Used in conjunction with therapies for treating external habits, very low calorie diets can supplement the effectiveness of these therapies.

In addition, if the subject has other physiological conditions that aggravate possible side effects of the stimulators of the implicit memory, offsetting medications such as β-blockers, which reduce heart rate, lower blood pressure, and ameliorate hypertension may be added to the protocol. Typical β-blockers which may be provided to ameliorate hypertension include atenolol (Tenormin), usually in dosages of 12.5–50 mg.

Thus, stage I involves, in general, stimulation of the implicit memory using appropriate compounds that stimulate amine neurotransmitters associated with the sympathetic nervous system supplemented with additional medications if desirable. The duration of stage I will vary from subject to subject. It may be as short as 1–3 weeks but may extend longer.

Stage II, which provides the basis for long-term control, continues the administration of stimulators of the implicit memory as done in stage I. The dosages and protocols for administration of these stimulators may be identical to that of stage I or may be modified according to the response perceived in the subject. In addition, medications which are used to control adverse effects of the primary effectors of implicit memory activity may also be used. Thus, for example, for hypertension, the administration of β-blockers may be continued.

Stage II differs from stage I in that a component of psychological and supportive therapy is added. Such therapies can be adapted to apply to non human animals as well. Most auxiliary medicaments are typically dropped. Conventional psychological and supportive treatment modalities are employed. These modalities are designed to affect the explicit memory and provide the basis for the deliberate recall of recent events that will be employed in stage III to result in permanent behavior modification. The psychological and supportive therapy may be as simple as consultations with the attending physician or may be more formal in nature, such as psychiatric treatment. For humans, generally a professional will provide this psychological and supportive therapy, although this could also be achieved through group counseling or intervention with respect to a care provider or other individual or individuals who routinely or often or sporadically interact with the subject of treatment. This is often the case where the subject is a nonhuman animal. In addition to professional interaction with the nonhuman animal, the professional or other intervention may be with respect, for example, to the owner of the animal who, in turn, by alteration of his/her behavior toward the subject, effects this psychological support.

The duration of stage II is also variable, but is typically several months to more than two years, most typically approximately 4–8 months. This stage is most susceptible to external influences, and the duration and intensity of the psychological and supportive component will vary depending in the case of human subjects, on the other circumstances in which the subject finds himself or herself. There is no theoretical upper limit to the duration of this stage, and Stage III can begin at any time, provided the effect of Stage II has been accomplished.

In stage III, the transfer of the behavior placed into explicit memory in stage II into the implicit memory occurs. In stage III, stimulation of the implicit memory is continued as in stage II, with suitable variation in dosage and regimen if indicated. Stage III involves the addition of administration of an acetylcholine esterase (AChase) inhibitor such as donepezil. Other currently available AChase inhibitors include tacrine and pyridostigmine bromide. Any AChase inhibitor or combination is within the scope of the invention. In stage III, both the implicit and explicit memory are stimulated, thus mimicking REM sleep. During this stage, the replacement of the learned behavior from stage II into the implicit memory is accomplished. The duration of stage III also varies from subject to subject, but is typically on the order of 6–12 months; stage III is continued until successful results are achieved.

Once the three stages are completed, the protocol is successful in a permanent alteration of behavior. The protocol is apparently successful in treating over 1400 subjects with behavior characteristics that include overeating, smoking tobacco, chewing tobacco, alcoholism, drug use, gambling, repetitive motion disorder and fatigue, who have either completed all stages of the treatment or are currently in stage II.

As will be apparent from the foregoing, the timing of stage I, stage II and stage III is quite variable depending on factors not necessarily under the control of the practitioner. The duration of any particular stage is dependent on, for example, the level of social support available to the subject, whether or not there are multiple addictions, the presence or absence of physical or psychological problems, and the like. Thus, although suggested durations are provided above, it is anticipated that such times will vary widely. Determination of the appropriate timing for each stage is well within ordinary skill of the practitioner.

The examples below illustrate typical protocols useful in the invention. In addition, the following dosages are typical as a preferred embodiment:

for phentermine (Adipex-P 37.5) one-half pill or one pill daily; this product contains 30 mg phentermine per pill;

for fenfluramine, one-quarter, one-half, or (rarely) one pill daily of a 20-mg tablet;

for citalopram (Celexa), one-fourth or one-half pill daily of a 20-mg tablet (if the subject indicates use of a serotonin uptake inhibitor, one pill daily may be prescribed);

for donepezil (Aricept), one-fourth to one-half pill daily as a 5-mg tablet.

The following examples are intended to illustrate but not to limit the invention.

EXAMPLE 1

Protocol for Overcoming Smoking

The following protocol is suitable for a subject of normal size and weight not suffering from hypertension or heart failure.

Stage I: 10 mg fenfluramine plus 30 mg phentermine daily for 2 weeks. The administration of these drugs is accompanied by a daily administration of 10 mg citalopram and 0.1–0.4 mg clonidine. The clonidine is administered as a transdermal patch. The subject is also provided a low dose (7 mg) nicotine patch.

Stage II: 10 mg fenfluramine/30 mg phentermine daily plus 10 mg citalopram daily for 6 months. Stage II also employs weekly 1-hour sessions with a psychotherapist. The duration of stage II is 12 months.

Stage III: 10 mg fenfluramine/30 mg phentermine plus 10 mg citalopram daily plus 2.5 mg donepezil daily. This regimen is continued for 6–12 months.

EXAMPLE 2

Protocol for Withdrawing from Alcohol

The following protocol is suitable for a subject of normal size and weight not suffering from hypertension or heart failure.

Stage I: 7 mg fenfluramine plus 25 mg phentermine daily for 3 weeks. The administration of these drugs is accompanied by a daily administration of 15 mg citalopram and 0.4 mg clonidine. The clonidine is administered as a transdermal patch. The subject is also provided a low dose of benzodiazapine.

Stage II: 7 mg fenfluramine/25 mg phentermine daily plus 15 mg citalopram daily for 6 months. Stage II also employs weekly 1-hour sessions with a psychotherapist. The duration of stage II is 4 months.

Stage III: 7 mg fenfluramine/25 mg phentermine plus 15 mg citalopram daily plus 3.0 mg donepezil daily. This regimen is continued for 6–12 months.

EXAMPLE 3

Protocol for Withdrawing from Cocaine Addiction

The following protocol is suitable for a subject of normal size and weight not suffering from hypertension or heart failure.

Stage I: 15 mg fenfluramine plus 25 mg phentermine daily for 3 weeks. The administration of these drugs is accompanied by a daily administration of 5 mg citalopram and 0.4 mg clonidine. The clonidine is administered as a transdermal patch.

Stage II: 10 mg fenfluramine/10 mg phentermine daily plus 10 mg citalopram daily for 5 months. Stage II also employs daily 1-hour sessions with a psychotherapist. The duration of stage II is 18 months.

Stage III: 5 mg fenfluramine/10 mg phentermine plus 1.5 mg donepezil daily. This regimen is continued for 6–12 months.

EXAMPLE 4

Protocol for Acquisition of Normal Eating Habits

The following protocol is suitable for a subject of normal size and weight not suffering from hypertension or heart failure.

Stage I: 5 mg fenfluramine plus 15 mg phentermine daily for 2.5 weeks. The administration of these drugs is accompanied by a daily administration of 0.2 mg clonidine. The clonidine is administered as a transdermal patch. The subject is also provided a Nutrimed™ diet regimen.

Stage II: 5 mg fenfluramine/15 mg phentermine 3× per week plus 5 mg citalopram weekly for 8 months. Stage II also employs weekly 1-hour sessions with a psychotherapist. The duration of stage II is 20 months.

Stage III: 5 mg fenfluramine/15 mg phentermine 3× per week plus 3.0 mg donepezil daily. This regimen is continued for 8 months.

EXAMPLE 5

Protocol for Overcoming Compulsive Gambling

The following protocol is suitable for a subject of normal size and weight not suffering from hypertension or heart failure.

Stage I: 10 mg fenfluramine plus 30 mg phentermine daily for 1 week. The administration of these drugs is accompanied by a daily administration of 10 mg citalopram.

Stage II: 10 mg fenfluramine/30 mg phentermine 5× per week plus 10 mg citalopram 5× per week for 4 months. Stage II also employs bi-weekly 1-hour sessions with a psychotherapist. The duration of stage II is 4 months.

Stage III: 10 mg fenfluramine/30 mg phentermine plus 5 mg citalopram daily plus 2.0 mg donepezil daily. This regimen is continued for 9 months.

EXAMPLE 6

Protocol for Overcoming Fatigue

The following protocol is suitable for a subject suffering from hypertension.

Stage I: 10 mg fenfluramnine plus 30 mg phentermine daily for 2 weeks. The administration of these drugs is accompanied by a daily administration of 5 mg citalopram and 10 atenolol.

Stage II: 10 mg fenfluramine/30 mg phentermine daily plus 5 mg citalopram daily for 4 months. Stage II also employs semi-weekly 1-hour sessions with a psychotherapist. The duration of stage II is 4 months.

Stage III: 10 mg fenfluramine/30 mg phentermine plus 5 mg citalopram daily plus 2.5 mg donepezil daily. This regimen is continued for 6–12 months.

EXAMPLE 7

Protocol and Results with Patient I.O.

Longstanding patient in my practice who at age 44 developed a viral illness followed by chronic fatigue. This problem persisted, numerous evaluations and consultations were obtained, in excess of 20 physicians were consulted, and the patient was followed for nine months in a major medical center with the diagnosis of chronic Lyme disease. Prior to this her symptoms included a compendium of mild lifelong autonomic dysfunction including chronic bladder and urethral problems which necessitated urological surgery in the distant past. She had not retired from work but had taken long leaves of absence and found it difficult to keep up her normal work schedule as a social worker, something she had done for many years. In the past for her autonomic dysfunction she had been placed on Depakote, Wellbutrin, and amitriptyline and she was on this when she became ill.

Her other medical problems included mitral valve prolapse with click and no murmur but no symptoms, a history of endometriosis, occasional kidney stones, and an ovarian cyst.

I began treatment nine months after the diagnosis of Lyme Disease with Adipex-P 37.5 mg one-half p.o. b.i.d., Celexa 10 mg. q.d., fenfluramine 10 mg q.d., and Aricept one-half q.d. Within two days the patient felt that her life had been transformed back towards its normal status. Therapy was begun on May 26, 1999. On Jun. 1, 1999 over the phone the patient was reduced to Adipex-P 37.5 one-half q.a.m., Celexa one-quarter q.a.m., and Aricept one-quarter q.a.m., fenfluramine was reduced to one-quarter of a pill as well. The patient did note some difficulty sleeping and her Elavil was switched from one-half pill to a full pill at night. At the end of June her medicines were kept to the same amount but switched to an every-other-day regime. By the end of July they had been weaned down to every fourth day. She was still on 12.5 mg of Elavil or one-half pill and some minocin for acne, Wellbutrin from her psychiatrist, and Zithromax, and antibiotic started by other physicians for the treatment of Lyme disease. This is something that I advised her to discontinue, but she continued because of the concerns of the diagnosis. The patient has had elective surgery and is doing well on q.4 day medication.

EXAMPLE 8

Protocol and Results with Patient J.L.

This gentleman has been a patient in this practice for many years. His medical problems are extremely long-lived and include chronic depression, severe obesity, hypertension, stasis dermatitis, and venous insufficiency of the lower extremities, and seborrhea. His depression was related historically to the fact that he was adopted and has never developed a good sense of self. His bilateral stasis dermatitis from chronic thrombophlebitis was very severe and interrupted his work on a frequent basis. He was 5'8½" tall and frequently unmeasurable at over 350 lb. Various attempts to get weight off him were successful, but none on a consistent basis. Sleep apnea was diagnosed and he was using a CPAP mask, high protein/low carbohydrate diets were mildly successful with approximately a 30 or 40 lb weight loss but they did not hold. The patient would occasionally become disillusioned with therapy and his physicians and withdraw, but would eventually return.

In August 1995 he was started on Ionamin 30 mg q.d., fenfluramine 20 mg q.d., and Zoloft 25 mg q.d. In addition he was taking Lasix, Zaroxolyn and potassium for the control of his severe edema and leg pain. He was also using the CPAP machine. His weight was not measurable on my office scales as it was in excess of 350 lb.

The patient did remarkably well with consistent weight loss. December 1997 he was in my office weighing 245 lb. and we agreed that he had lost in excess of 100 lb by that time. He had an incidental rotator cuff injury which necessitated some surgery. His medicines were withdrawn for that, but quickly restarted. The adjustment in trials of medications continued as did his weight control and weight loss. His legs became less uncomfortable and he missed no work from chronic pain.

In October 1998 he had an elective inguinal herniorrhaphy which was uncomplicated. At that time he weighed 252 lb with a normal blood pressure. At his insistence Meridia and Adalat were attempted. Since he did not feel as comfortable on these, his medicines were switched back to Adipex-P 37.5 mg one-half p.o. b.i.d., Celexa 20 mg one-half MWF, and Adalat 30 one daily. Aricept was started May 1999 with an attempt to continue weight loss plus get his medicines to a less frequent basis. To augment the weight loss the patient was started on Nutrimed three times daily plus a regular dinner. The reason for the Nutrimed was that as a result of the Meridia his weight had gone up to 264¼ lb.

By phone, the patient is losing weight and is in the 240s; he will be seen later on this month. The patient is looking forward to cosmetic surgery when he gets his weight close to 200 lb because the massive weight change has stretched his skin.

EXAMPLE 9

Protocol and Results with Patient N.C.

This gentleman has been in the practice for several years. His medical problems surround a cardiomyopathy with a low cardiac output state and heart failure. He also has a history of hypertension, hypothyroidism on therapy, and morbid obesity. He is 5'9", averaging around 237 lb and his medications included ACE inhibitors, thyroid replacement, aspirin, and vitamins.

The patient was started on Ionamin and Zoloft in April 1996. His medications were Ionamin 15, Zoloft 25, Synthroid 0.125, and Vasotec 10, aspirin one tablet q.d. Medication alterations continued over the next several months with increasing Ionamin to 30 mg. Hytrin was added at 2 mg because of prostatic symptoms and in November Pondimin was added. The patient's weight at that time was 230 lb but not decreasing.

In July 1997 he weighed 217 lb, his blood pressure was improved, his cardiac output had improved by echocardiography and his chamber size had reduced. This was interpreted as improvement in his cardiomyopathy and heart failure. The patient's opinion was that he was doing great. Pondimin or fenfluramine was withdrawn and with its restricted use, the patient's weight went up, but his improvement persisted on Synthroid, Hytrin, Vasotec, and aspirin.

Throughout 1998 his weight unfortunately increased and at 233 lb he started to become fatigued. Adipex-P 37.5 one-half was added to his medications. Celexa 10 mg was added twice weekly in December 1998 plus empiric Aricept one-quarter pill MWF. There was essentially no improvement in the absence of the fenfluramine.

Although his weight did not change significantly, in June 1999, he weighed 235 lb. He claimed he could not adhere to his diet and felt he would try anything to get back into control to avoid reoccurrence of heart failure. His medications were the following: Synthroid, aspirin, and Vasotec were unchanged, atenolol 12.5 mg, Adipex-P 37.5 one-half, Zoloft 25 mg, Aricept 1.25 mg and fenfluramine one-quarter pill or 5 mg, Hytrin 5 mg was used at bedtime. The patient's response was excellent with a decrease of his weight in one month to 224½, the next month to 218 and a return of his sense of vigor and energy. His cardiac index was remeasured and was even more improved than previously. His dosages are being split off to an alternate-day schedule and will be adjusted to start decreasing even further.

EXAMPLE 10

Protocol and Results with Patient J.S.

This longstanding patient was first seen in 1988 for fibromyalgia. She is also bothered by chronic low back pain, mitral valve prolapse, sleep disturbance, a family history of coronary disease, and obesity. She is 5'8" tall, 205½ lb. Up until 1995 the patient had been tried on numerous therapies with moderate success. Her problem list contained the additional diagnoses of GERD, carpal tunnel syndrome, suspected mitral valve prolapse, and acne rosacea.

Her medication list included Synthroid, Estratest, Klonopin, Prilosec, Limbitrol, Provera, Premarin and Zostrix cream. She had been tried on chronic doxycycline therapy for three months without success. She frequented health food stores, as well as chiropractors for relief. She could not work and the level of time she could be out of bed at any one time was approximately three hours.

Although greatly fearful of potential long-term problems, the patient finally agreed to the institution of a change in her medications and started therapy which was a major change in her medicines December 1995. Ionamin 30 mg (phentermine), fenfluramine 20 mg, and Zoloft 25 mg were started December 1995. At that time the patient's weight was in the mid 180s. Her other medications were continued.

Over the succeeding three years the patient was greatly improved. She felt well, lost substantial amounts of weight, had medications diminished to infrequent doses, and started to live, in her words "a normal life." Within a year she was on every-third-day medications and for reasons that are not abundantly clear she made a decision in 1996 to discontinue the fenfluramine. This was an independent patient-initiated decision. In August 1998 I suggested that she consider the use of Aricept and this was started at 2.5 mg Monday, Wednesday, and Friday. The patient felt much better and agreed to further reductions in her medicines to take them less frequently.

On therapy the patient has lost approximately 25 lb to date although at times this was slightly greater. There seems to be a range of her weight and I think 25 is an accurate number. In July 1999 she weighed 161 lb. Her vital signs were normal and she was not only comfortable, but quite active.

Her current medications are atenolol 25 mg q.a.m., Prempro 2.5 mg one q.a.m., Ionamin 15 mg q.a.m., Prilosec 20 mg every fourth day, Aricept one-quarter pill MWF, and Limbitrol 5/12.5 at bedtime.

The patient's chronic fatigue has not completely disappeared but exists as perhaps 20% of its original and she otherwise has no other substantial constitutional complaints from her fibromyalgia.

EXAMPLE 11

Protocol and Results with Patient N.K.

First evaluated this 5'4", ectomorphic, single woman who was 46 years old at the time. She was nulliparous by choice but also had, on evaluation, acne vulgaris plus acne rosacea, low back pain, and a congenital vascular malformation with superficial thrombophlebitis of both thighs. She had occasional palpitations as well.

On Nov. 9, 1998 the patient returned seeking help because of aching pain in her legs, a fear of recurrence of the thrombophlebitis, and an absence of energy. She was started on Celexa 10 mg, Adipex-P 37.5 one-half tablet, and atenolol 25 mg all in the morning. Although only mildly overweight at 143 lb, by August 1999 she weighed 127 lb, had a resolution of her leg aches, a normal sense of energy, and had weaned her dosage to Celexa, Adipex, and Aricept 1.25 mg three times weekly. The atenolol was discontinued as the patient lost weight and her energy returned. At no time did she have palpitations.

The patient was seen in August 1999 and was starting to stretch her doses out to every three days/every four days/every five days in a sequential fashion. She will keep in touch with me as she will take each instruction for four doses and then go to the next. The patient accomplished 12.5% weight reduction plus resolution of her symptoms.

EXAMPLE 12

Protocol and Results with Patient J.S.

Sixty-six year old man with sudden onset of numbness right side of body in Guyana 1973. Numerous evaluations including NIH and Neurology Center yielded no help despite trials with Neurontin, Elavil, Tegretol, Dilantin, antidepressants, and narcotics. Best therapy was ethanol which the patient consumed day long averaging two to four mixed drinks per day taken from the early a.m. until evening. Diagnosis was thalamic pain syndrome.

Other medical problems: borderline hypertension, obesity secondary to ETOH, hemorrhoids, and remote short-lived cigarette smoking.

Recurrent objective physical examination findings include mild impairment of graphesthesia on the right hand and dysesthesia induced by light touch of the hairs on the right limbs and face by hot and cold objects.

At the time therapy started the patient was taking either hydrocodone/APAPE 7.5/500 as needed or Percocet. Both were not effective but did make him sleep better secondary to lethargy. Therapy was started with Adipex-P 37.5 one-half p.o. bid., fenfluramine 10 mg p.o. q.a.m., Celexa 10 mg p.o. q.a.m., Nutrimed three times daily plus dinner for nutritional support (Nutrimed is a high protein, low carbohydrate semi-starvation fast), Librium 30 mg q.d. because of the discontinuation of alcohol, atenolol 25 mg q.a.m. Treatment started July 1999.

Response: Librium was discontinued by day three because the 30 mg dose was causing mild sleepiness. This wore off quickly. There were no withdrawal phenomena.

The patient noted marked improvement in energy level and described his pain as a markedly diminished yet persistent presence but something for which he needed no medication. It neither bothered him enough to seek alcohol or other pain medication. The doses of medicines were adjusted as the patient's weight and blood pressure came down. By mid-August, approximately five weeks into therapy, the patient was still on Nutrimed and Adipex but the fenfluramine was diminished to one-quarter of a pill or 5 mg. The atenolol was discontinued and the patient was encouraged to exercise. Of note, he had marked weight loss and stability of his blood pressure in the normal range. Because of the increase in physical activity, it was suggested to combine glucosamine and chondroitin sulfate and a low dose of creatine phosphate. These are for joint support and energy with respect to his new found ability to exercise and the desire to keep him in that mode. It is anticipated in the future to add Aricept.

EXAMPLE 13

Protocol and Results with Patient R.M.

This patient has been in this particular practice for decades. At the time of treatment of her cigarette smoking, September 1995, she had the following medical problems: recurrent low back pain, fibrocystic breast disease, irritable bowel syndrome with bloating, intermittent headaches, and a chronic anxiety disorder. Her medications included Xanax on a daily basis, Lodine, and Excedrin for headaches which averaged two pills per day.

After approximately a month of discussion the patient agreed to start a nicotine patch, Ionamin (phentermine), Pondimin (fenfluramine), and Zoloft (sectraline HCl) on a three-time-a-week basis. The nicotine replacement patch made the patient symptomatic and she withdrew from therapy but further consultation identified the problem and the patch was diminished to 7 mg q.d. The patient lost weight on this plan and immediately stopped smoking. About a month into therapy and with good success, including weight loss and the cessation of smoking, the patient, for some unexplained reason, discontinued all medical therapy. She claimed she thought she was cured so she could go on her own. Within several weeks she started her habits again and re-presented to my office in March 1996. She was restarted on Ionamin, Pondimin, and Zoloft on a daily basis and then quickly switched to Monday, Wednesday, Friday. In addition, she was started on the moderate dose of the patch. The patient again intermittently took the medicines and began to smoke. With recurrent episodes of bronchitis in the spring of 1996 the patient once again re-presented and promised to stay on therapy. By August of 1996 she was taking her Ionamin, Pondimin and Zoloft on an every-three-day basis. She used the nicotine patch as a psychological crutch; whenever she felt she needed to smoke she would use it for a few days in the low dose size. Her other medical problems improved, including digestion and headaches.

A physical examination in August 1996 yielded the possibility that some of the patient's problems in terms of follow-through may be related to the lethargy caused by peri-menopause. The patient was 57 years old but had menstruated into her mid 50s. She was started on Estratest with a marked improvement and from that point on no failures in terms of her desire to stop smoking and to continue. With the removal of fenfluramine from the market the patient's medicines were adjusted. In January 1998 she was taking Ionamin 15 mg, Prozac 10 mg MWF, Estratest, and an occasional Tranxene. She was not smoking. Her weight was 119 lb. but she desired, because of her body habitus, to weigh a little bit less. My opinion by BMI was this was not unreasonable.

Although there have been some shifts in her medication the patient to date is doing extremely well. In July 1999 she weighed 111½ lb. She is taking atenolol 25 mg, Adipex-P 37.5 one-half, and Zoloft one-half MWF basis. It is intended to start Aricept later on this year.

What is claimed is:

1. A method to alter a habitual behavior in a subject which method comprises the steps of
    a) administering to said subject an effective amount of at least one medicament that stimulates implicit memory for a time period sufficient to stimulate said implicit memory; followed by
    b) administering to said subject at least one medicament which stimulates implicit memory along with treating said subject with or causing said subject to be treated with psychotherapeutic or psychological support stimuli for a period sufficient to affect the explicit memory of said subject so as to learn a desired behavior; followed by
    c) administering to said subject an effective amount of at least one medicament that stimulates the implicit memory of said subject and at least one medicament which stimulates the explicit memory of said subject for a period sufficient to transfer the behavior learned from step b) from the explicit memory into the implicit memory.

2. The method of claim 1 wherein the subject is human.

3. The method of claim 2 wherein said at least one medicament to stimulate the implicit memory comprises phentermine, fenfluramine and citalopram.

4. The method of claim 2 wherein the medicament to stimulate the explicit memory comprises donepezil.

5. The method of claim 2 wherein the subject is at risk or is suffering from hypertension or tachycardia and step a) further includes administering to said subject a β-blocker.

6. The method of claim 2 wherein the β-blocker is atenolol.

7. The method of claim 2 wherein the subject is at risk for or is suffering from repetitive motion disorders and wherein step a) further includes administering an $\alpha_2$ adrenergic receptor agonist.

8. The method of claim 7 wherein said agonist is clonidine.

9. The method of claim 2 wherein said subject is to be cured of smoking and wherein step a) further includes administering a nicotine patch.

10. The method of claim 2 wherein the subject is to be cured of alcoholism and step a) further includes administering benzodiazapine.

11. The method of claim 1 wherein the duration of step a) is about 1–3 weeks, of step b) is about 4–8 months, and of step c) is about 6–12 months.

* * * * *